US006911569B1

(12) United States Patent
Munson et al.

(10) Patent No.: US 6,911,569 B1
(45) Date of Patent: Jun. 28, 2005

(54) SULFUR RESISTANT ADSORBENTS

(75) Inventors: Curtis L. Munson, Oakland, CA (US); Ralph T. Yang, Ann Arbor, MI (US)

(73) Assignees: The Regents of the University of Michigan, Ann Arbor, MI (US); Chevron U.S.A., Inc., San Francisco, CA (US)

( * ) Notice: Subject to any disclaimer, the term of this patent is extended or adjusted under 35 U.S.C. 154(b) by 457 days.

(21) Appl. No.: 09/632,891

(22) Filed: Aug. 7, 2000

(51) Int. Cl.$^7$ ................................................ C07C 7/12
(52) U.S. Cl. ........................ 585/820; 585/809; 585/810; 585/826; 585/829
(58) Field of Search ............................... 585/809, 810, 585/820, 826, 829

(56) References Cited

U.S. PATENT DOCUMENTS

| | | |
|---|---|---|
| 2,606,938 A | 8/1952 | Robinson |
| 2,685,607 A | 8/1954 | Pevere et al. |
| 2,882,243 A | 4/1959 | Milton |
| 2,882,244 A | 4/1959 | Milton |
| 3,130,007 A | 4/1964 | Breck |
| 3,189,658 A | 6/1965 | Quinn |
| 3,211,644 A | 10/1965 | Clark |
| 3,221,073 A | 11/1965 | Davis et al. |
| 3,243,471 A | 3/1966 | Stern |
| 3,311,671 A | 3/1967 | Baker |
| 3,331,882 A | 7/1967 | Mattox |
| 3,350,472 A | 10/1967 | DeFeo |
| 3,409,692 A | 11/1968 | Long et al. |
| 3,785,122 A | 1/1974 | Yatsurugi et al. |
| 3,992,471 A | 11/1976 | Priegnitz |
| 4,019,880 A | 4/1977 | Rabo et al. |
| 4,717,398 A | 1/1988 | Pearce |
| 4,917,711 A | 4/1990 | Xie et al. |
| 5,268,023 A | 12/1993 | Kirner |
| 5,365,011 A | 11/1994 | Ramachandran et al. |
| 5,551,257 A | 9/1996 | Jain |
| 5,554,208 A | 9/1996 | Mullhaupt et al. |
| 5,656,064 A | 8/1997 | Golden et al. |
| 5,672,196 A | 9/1997 | Acharya et al. |
| 5,675,052 A | 10/1997 | Menon et al. |
| 5,713,984 A | 2/1998 | Monnot et al. |
| 5,744,687 A | 4/1998 | Ramachandran et al. |
| 6,042,797 A * | 3/2000 | Ogawa et al. ............ 423/213.2 |
| 6,063,723 A | 5/2000 | Miller |

FOREIGN PATENT DOCUMENTS

| | | |
|---|---|---|
| EP | 0 056 197 | 7/1982 |
| EP | 0 354 316 | 2/1990 |
| GB | 1356420 | 6/1974 |
| GB | 1509586 | 5/1978 |
| WO | WO 00/24695 | 5/2000 |

OTHER PUBLICATIONS

"New Sorbents for Olefin/paraffin separations by adsorption via X–Complexation", Joel Padin and R–. T. Yang No. 3, pp. 1–22.*
Tedder, J.M., A. Nechvatal, A.H. Jubb, *Basic organic chemistry, Part 5: Industrial Products*, Chapter 3.2, pp. 53–60, (1975).
"Materials and Interfaces *Ab Initio* Molecular Orbital Study of Adsorption of Oxygen, Nitrogen, and Ethylene on Silver–Zeolite and Silver Halides", N. Chen and R.T. Yang, *Ind. Eng. Chem. Res.* 1996, vol. 35, pp. 4020–4027.
"New Sorbents for Olefin/Paraffin Separations by Adsorption via π–Complexation", R.T. Yang and E.S. Kikkinides, *AIChE Journal*, Mar. 1995, vol. 41, No. 3, pp. 509–517.
"Spontaneous Monolayer Dispersion of Oxides and Salts onto Surfaces of Supports: Applications to Heterogeneous Catalysis", You–Chang Xie and You–Qi Tang, *Advances in Catalysis*, vol. 37, pp. 1–43.
"Olefin/Paraffin Separations by Adsorption:π–Complexation vs. Kinetic Separation" Salil U. Rege, Joel Padin, and Ralph T. Yang, *AIChE Journal*, Apr. 1998, vol. 44, No. 4, pp. 799–809.
"Separation, Modification of Resin–Type Adsorbents for Ethane\Ethylene Separation," Zhongbiao Wu, Sang–Sup Han, Soon–Haeng Cho, Jong–Nam Kim, Kuck–Tack Chue, and Ralph T. Yang, *Ind. Eng. Chem. Res.* 1997, vol. 36, pp. 2749–2756.
Gas Separation and Purification by Polymeric Adsorbents: Flue Gas Desulfurization and $SO_2$ Recovery with Styrenic Polymers:, E.S. Kikkinides and R.T. Yang, *Ind. Eng. Chem. Res.* 1993, vol. 32, pp. 2365–2372.

* cited by examiner

*Primary Examiner*—Walter D. Griffin
*Assistant Examiner*—Tam M. Nguyen
(74) *Attorney, Agent, or Firm*—Dierker & Associates

(57) ABSTRACT

Sulfur resistant/tolerant adsorbents useful for separating olefins from paraffins in a cracked gas stream including hydrogen sulfide. The method comprises the steps of contacting the gaseous mixture with an adsorbent which preferentially adsorbs the alkene, at a selected temperature and pressure, thereby producing a non-adsorbed component and an alkene-rich adsorbed component; the adsorbent comprising a carrier having a surface area, the carrier having been impregnated with a silver compound by incipient wetness, the silver compound releasably retaining the alkene; and changing at least one of the pressure and temperature to thereby release the alkene-rich component from the adsorbent. The adsorbent substantially maintains its adsorbent capacity and preference for the alkene in the presence of the sulfur compound. Sulfur resistant/tolerant adsorbents useful for selectively separating dienes from a mixture, particularly one containing mono-olefins and hydrogen sulfide, are also disclosed.

48 Claims, 11 Drawing Sheets

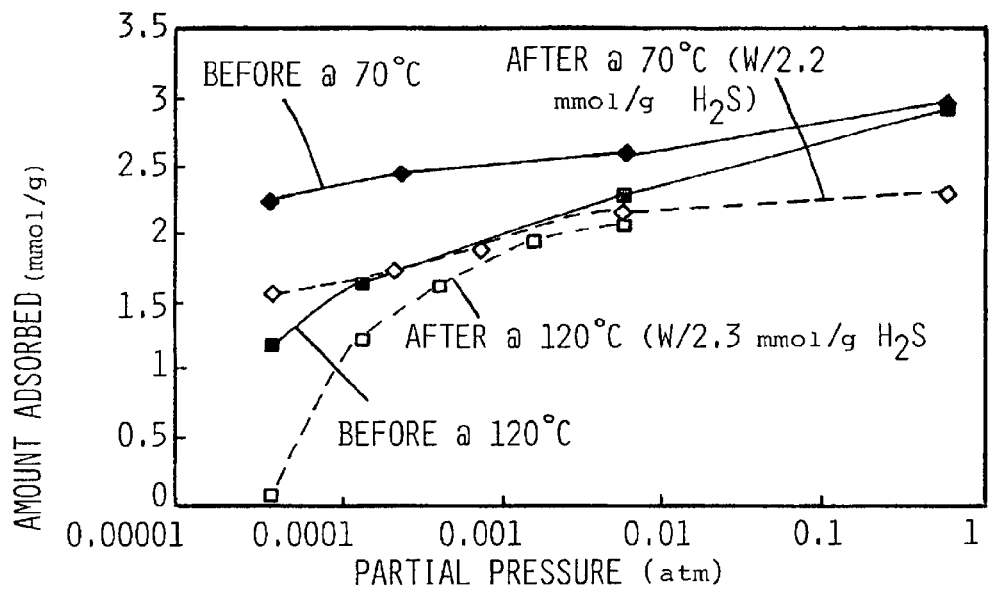
FIG-12A
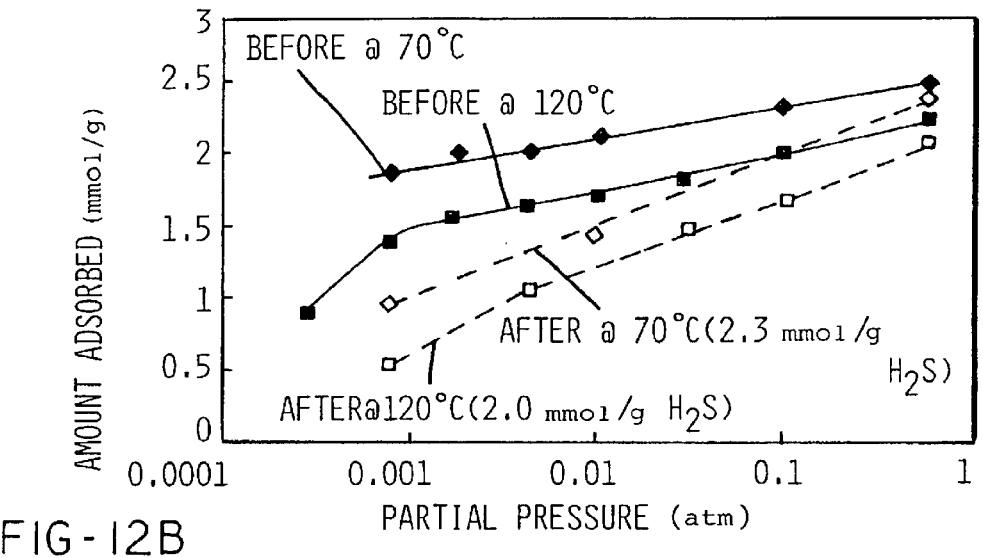
FIG-12B
|  | 1,3-BUTADIENE | 1-BUTENE |
|---|---|---|
| BEFORE H$_2$S EXPOSURE | 24-29 KCAL/mol | 16-22 KCAL/mol |
| AFTER H$_2$S EXPOSURE | 7-11 KCAL/mol | 6-7 KCAL/mol |
FIG-12C

SULFUR RESISTANT ADSORBENTS

CROSS-REFERENCE TO RELATED APPLICATIONS

This application is related to co-pending U.S. application Ser. No. 09/177,256, filed Oct. 22, 1998, and to U.S. application Ser. No. 09/179,667, filed Oct. 27, 1998, now U.S. Pat. No. 6,215,037, each of which applications is incorporated herein by reference in its entirety.

BACKGROUND OF THE INVENTION

The present invention relates generally to adsorbents for selectively separating olefins from paraffins, and to adsorbents for selectively separating dienes from a mixture, particularly one containing mono-olefins. More particularly, the present invention relates to such adsorbents which are resistant to and/or tolerant of sulfur poisoning.

Petroleum is an extremely complex mixture and consists predominantly of hydrocarbons, as well as compounds containing nitrogen, oxygen, and sulfur. Most petroleums also contain minor amounts of nickel and vanadium. The chemical and physical properties of petroleum vary considerably because of the variations in composition.

The ultimate analysis (elemental composition) of petroleum tends to vary over relatively narrow limits—carbon: 83.0 to 87.0 percent; hydrogen: 10.0 to 14.0 percent; nitrogen: 0.1 to 1.5 percent; oxygen: 0.1 to 1.5 percent; sulfur: 0.1 to 5.0 percent; metals (nickel plus vanadium): 10 to 500 ppm.

Crude oils are seldom used as fuel because they are more valuable when refined to petroleum products. Distillation separates the crude oil into fractions equivalent in boiling range to gasoline, kerosine, gas oil, lubricating oil, and residual. Thermal or catalytic cracking is used to convert kerosine, gas oil, or residual to gasoline, lower-boiling fractions, and a residual coke. Petrochemical intermediates such as ethylene and propylene are primarily produced by the thermal cracking of light hydrocarbon feedstocks in the presence of steam. Catalytic reforming, isomerization, alkylation, polymerization, hydrogenation, and combinations of these catalytic processes are used to upgrade the various refinery intermediates into improved gasoline stocks or distillates. The major finished products are usually blends of a number of stocks, plus additives.

Gasoline is a complex mixture of hydrocarbons that distills within the range 100 to 400° F. Commercial gasolines are blends of straight-run, cracked, reformed, and natural gasolines. Straight-run gasoline is recovered from crude petroleum by distillation and contains a large proportion of normal hydrocarbons of the paraffin series. Cracked gasoline is manufactured by heating crude-petroleum distillation fractions or residues under pressure, or by heating with or without pressure in the presence of a catalyst. Heavier hydrocarbons are broken into smaller molecules, some of which distill in the gasoline range. Reformed gasoline is made by passing gasoline fractions over catalysts in such a manner that low-octane-number hydrocarbons are molecularly rearranged to high-octane-number components. Many of the catalysts use platinum and other metals deposited on a silica and/or alumina support. Natural gasoline is obtained from natural gas by liquefying those constituents which boil in the gasoline range either by compression and cooling or by absorption in oil.

Propylene is recovered as a by-product in the catalytic cracking of gas oils to gasoline. Catalytic cracking is a low-pressure process which normally operates at 450–600° C. with a strongly acidic catalyst containing a crystalline aluminosilicate (molecular sieve). Cracking of paraffinic components proceeds by a carbonium ion mechanism which has a β-fission step similar to that found for free radicals. Lower olefins are also recovered to a lesser extent from Fisher-Tropsch, thermal-cracking and coal-gasification units.

The presence of sulfur compounds is generally known to have deleterious effects in various petroleum refining processes. For example, in catalytic reforming, the catalyst used is often platinum supported on high-purity alumina. However, the platinum on the catalyst is seriously deactivated by sulfur compounds, and therefore the feedstock is desulfurized to less than 3 ppm by weight of sulfur before the reforming. See, for example, Tedder, J. M., A. Nechvatal and A. H. Jubb, *Basic Organic Chemistry Part 5: Industrial Products,* Chapter 3.2, "Preparation of Primary Petrochemicals: Reforming," pp. 53–60 (1975).

U.S. Pat. No. 6,063,723 issued to Miller also demonstrates that sulfur is known to have deleterious effects. The '723 patent discloses a sulfur tolerant zeolite catalyst for use in catalytic dehydrogenation of light paraffinic hydrocarbons. This catalyst is prepared such that it has a very specific alkali to aluminum ratio in the zeolite. Although this patent's disclosed sulfur tolerance is better than that of previously known catalysts, it is still only disclosed to be tolerant of sulfur in the range of up to 2 ppm sulfur, and more preferably up to 0.5 ppm sulfur.

Cracked gas streams include a blend of many components, including olefins, paraffins, $H_2$, $H_2S$, etc. The cracked gas streams are first subjected to caustic scrubbing in order to remove hydrogen sulfide. Then, it is necessary to separate olefins from paraffins in these streams in order to obtain a product rating. Conventional methods for such separation include multiple distillation runs, one of which removes, for example, $H_2$ and methane. Thereafter, the stream includes $C_2$'s and higher, mixed with olefins and paraffins. This stream is then distilled to separate the olefins from the paraffins. However, this distillation is very energy intensive and difficult to accomplish because of relatively close volatilities when alkene\alkane (olefin\paraffin) separation is required. For example, ethane\ethylene separation is carried out at about −25° C. and 320 psig (2.603 MPa) in a column containing over 100 trays, and propane\propylene separation is performed by an equally energy-intensive distillation at about 38° C. and 260 psig (1.8 MPa). It is evident that high capital costs and high operational costs are incurred in any cryogenic distillation approach.

Further, it is also very difficult to separate a diene from a mixture, particularly one containing mono-olefin. Purifying the mono-olefin, 1-butene, is particularly troublesome due to the closeness of its boiling point to that of 1,3-butadiene. In order to increase the purity of 1-butene, it is necessary to separate it from other hydrocarbons. Ordinarily, fractionation alone is cost prohibitive for completely separating 1,3-butadiene to achieve the desired purity of 1-butene in these mixtures. Presently, butadiene is separated from olefins and paraffins primarily by distillation with selective solvents and by absorption using solutions of absorbents. Extractive distillation is relatively energy-intensive, complex and not economical. There are several drawbacks, in that this puts water vapor and/or solvent vapor into the regenerated product. Further, metal salts often are instable in solution and will precipitate out of solution. Selective absorption with metal salt solution involves additional stages with recycling of streams between stages to remove water vapor and/or solvent vapor from the regenerated product. This method has the disadvantage of being energy-intensive and requiring handling and recirculating of solvent streams which themselves contain contaminants or are subject to degradation. Current processes for olefin\paraffin separation have not been sufficiently selective to economically achieve the desired result for purifying mixtures of unsaturated hydrocarbons.

Thus, it is an object of the present invention to provide adsorbents which would cost-effectively and successfully achieve separation of olefins from paraffins. It is a further object of the present invention to provide adsorbents which would cost-effectively and successfully achieve separation of dienes from mono-olefins. Still further, it is an object of the present invention to provide such absorbents which are advantageously resistant to and/or tolerant of sulfur poisoning.

SUMMARY OF THE INVENTION

The present invention addresses and solves the above-mentioned problems and meets the enumerated objects and advantages, as well as others not enumerated, by providing novel, sulfur resistant and/or tolerant adsorbents useful in a method of separating gaseous alkene selected from the group consisting of ethylene, propylene and mixtures thereof, from a gaseous mixture including the alkene and hydrogen sulfide, the hydrogen sulfide present in amounts normally present in conventional cracked gas streams. The method comprises the steps of contacting the gaseous mixture with an adsorbent which preferentially adsorbs the alkene, at a selected temperature and pressure, thereby producing a non-adsorbed component and an alkene-rich adsorbed component; the adsorbent comprising a carrier having a surface area, the carrier having been impregnated with a silver compound by incipient wetness, thereby resulting in a monolayer of the silver compound dispersed on substantially the entire surface area, the silver compound releasably retaining the alkene; and the carrier comprising a plurality of pores having a pore size greater than the effective molecular diameter of the alkene; and changing at least one of the pressure and temperature to thereby release the alkene-rich component from the adsorbent. The adsorbent advantageously and unexpectedly substantially maintains its adsorbent capacity and preference for the alkene in the presence of hydrogen sulfide.

Further novel, sulfur resistant and/or tolerant adsorbents are useful in a method for separating a diene from a mixture including the diene and hydrogen sulfide, the hydrogen sulfide present in amounts normally present in conventional cracked gas streams. The process comprises the step of contacting the mixture with an adsorbent which preferentially adsorbs the diene, at a selected temperature and pressure, thereby producing a non-adsorbed component and a diene-rich adsorbed component, wherein the adsorbent comprises an ion-exchanged zeolite selected from the group consisting of zeolite X, zeolite Y, zeolite LSX, and mixtures thereof, the zeolite having exchangeable cationic sites, and a majority, of the sites having silver cation or copper cation present, and wherein the preferential adsorption occurs by π-complexation, and further wherein the adsorbent advantageously and unexpectedly substantially maintains its adsorbent capacity and preference for the diene in the presence of the hydrogen sulfide.

BRIEF DESCRIPTION OF THE DRAWINGS

Other objects, features and advantages of the present invention will become apparent by reference to the following detailed description and drawings, in which:

FIG. 12a is an isotherm of 1,3-butadiene before and after $H_2S$ exposure;

FIG. 12b is an isotherm of 1-butene before and after $H_2S$ exposure;

FIG. 12c is a table showing calculated heat of adsorption of 1,3-butadiene and 1-butene before and after $H_2S$ exposure;

DETAILED DESCRIPTION OF THE PREFERRED EMBODIMENTS

Figure 1:
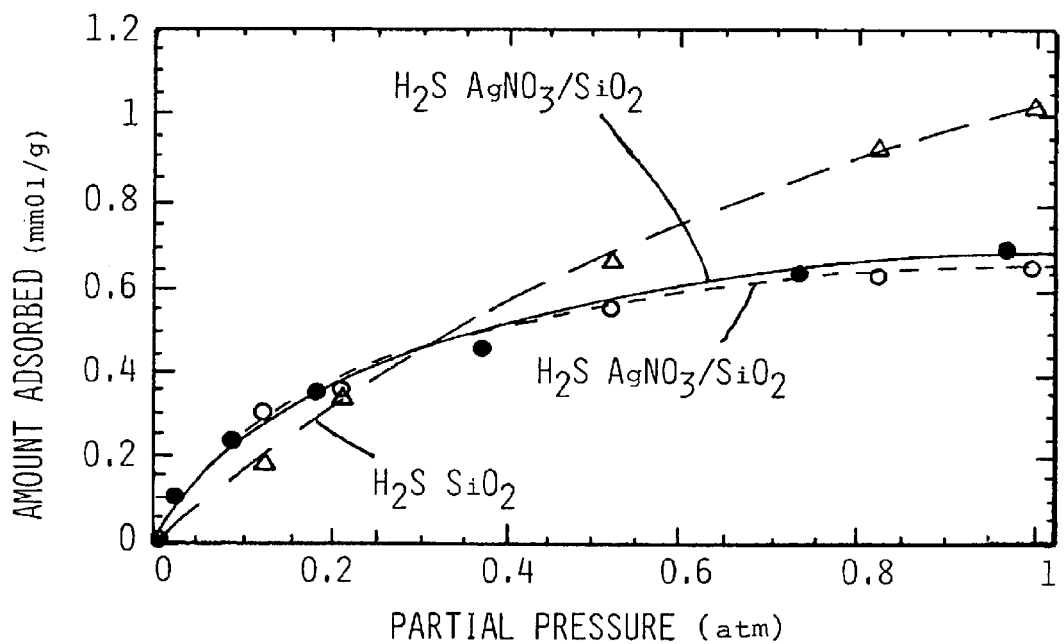
FIG. 1 is a graph showing comparison of $H_2S$ adsorption on $SiO_2$ and $AgNO_3/SiO_2$ at 70° C.

As disclosed hereinabove, it has been generally expected that adsorbents containing metal compounds would be irreversibly poisoned and rendered useless upon prolonged and/or extensive exposure to sulfur containing compounds, such as for example, hydrogen sulfide. However, in the present invention, novel adsorbents useful for cost-effective and highly successful separation of olefins from paraffins, and separation of dienes from a mixture (particularly one containing mono-olefins) have been unexpectedly and fortuitously discovered to be tolerant of and/or resistant to sulfur compounds. These inventive adsorbents have been shown to substantially maintain their selectivity and their adsorption capacity, even upon severe exposure to $H_2S$.

In one embodiment of the present invention, there is disclosed a novel method of separating gaseous alkene selected from the group consisting of ethylene, propylene and mixtures thereof, from a gaseous mixture including the alkene and a sulfur compound. The method comprises the step of contacting the gaseous mixture with an adsorbent which preferentially adsorbs the alkene, at a selected temperature and pressure, thereby producing a non-adsorbed component and an alkene-rich adsorbed component.

The adsorbent comprises a carrier having a surface area, the carrier having been impregnated with a silver compound by incipient wetness thereby resulting in a monolayer of the silver compound dispersed on substantially the entire surface area. The silver compound releasably retains the alkene; and the carrier comprises a plurality of pores having a pore size greater than the effective molecular diameter of the alkene.

It is to be understood that any suitable carrier may be used. However, in a preferred embodiment, the carrier has a BET surface area greater than about 50 square meters per gram and up to about 2,000 square meters per gram, and comprises a plurality of pores having a pore size greater than about 3 angstroms and up to about 10 microns. In a more preferred embodiment, the carrier is a high surface area support selected from the group consisting of refractory inorganic oxide, molecular sieve, activated carbon, and mixtures thereof. Still more preferred, the carrier is a refractory inorganic oxide selected from the group consisting of pillared clay, alumina and silica.

It is also to be understood that any suitable silver compound may be used. However, in a preferred embodiment, the silver compound is a silver (I) halide. In a more preferred embodiment, the silver compound is a silver salt, and the salt is selected from the group consisting of acetate, benzoate, bromate, chlorate, perchlorate, chlorite, citrate, fluoride, nitrate, nitrite, sulfate, and mixtures thereof.

In one exemplary embodiment of the present invention, the silver compound is silver nitrate ($AgNO_3$) and the carrier is silica ($SiO_2$).

The method of the present invention may further comprise the step of changing at least one of the pressure and temperature to thereby release the alkene-rich component from the adsorbent. It is to be understood that the pressures and temperatures used may be within a suitable range. However, in the preferred embodiment, the selected pressure of preferential adsorption is a first pressure, and the pressure of release is a second pressure less than the first pressure. In a more preferred embodiment, the first pressure is in a range of about 1 atmosphere to about 35 atmospheres, and the second pressure is in a range of about 0.01 atm to about 5 atm.

In the preferred embodiment, the selected temperature of preferential adsorption is a first temperature, and the temperature of release is a second temperature greater than the first temperature. In a more preferred embodiment, the first temperature is in a range of about 0° C. to about 50° C., and the second temperature is in a range of about 70° C. to about 200° C.

Without being bound to any theory, it is believed that the retaining of the alkene is accomplished by formation of π-complexation bonds between the silver compound and the alkene. Separation by π-complexation is a subgroup of chemical complexation where the mixture is contacted with a second phase, which contains a complexing agent. The advantage of chemical complexation is that the bonds formed are stronger than those by van der Waals forces alone, so it is possible to achieve high selectivity and high capacity for the component to be bound. At the same time, the bonds are still weak enough to be broken by using simple engineering operations such as raising the temperature or decreasing the pressure.

The π-complexation generally pertains to the main group (or d-block) transition metals, that is, from Sc to Cu, Y to Ag, and La to Au in the periodic table. These metals or their ions can form the normal σ bond to carbon and, in addition, the unique characteristics of the d orbitals in these metals or ions can form bonds with the unsaturated hydrocarbons (olefins) in a nonclassic manner. This type of bonding is broadly referred to as π-complexation, and has been considered for gaseous hydrocarbon separation and purification using cumbersome liquid solutions.

As demonstrated further hereinbelow, this novel adsorbent fortuitously and unexpectedly substantially maintains its adsorbent capacity and preference for the alkene in the presence of the sulfur compound. This is highly desirable, as this sulfur tolerant and/or resistant adsorbent (as well as the other novel adsorbents described hereinbelow) obviates step (s) conventionally necessary to desulfurize the cracked gas stream(s).

In a further embodiment, a novel method is disclosed for separating a diene from a mixture including the diene and a sulfur compound. The process comprises the step of contacting the mixture with an adsorbent which preferentially adsorbs the diene, at a selected temperature and pressure, thereby producing a non-adsorbed component and a diene-rich adsorbed component. The adsorbent comprises an ion-exchanged zeolite selected from the group consisting of zeolite X, zeolite Y, zeolite LSX, and mixtures thereof, the zeolite having exchangeable cationic sites, with silver cation or copper cation present at some or all of the exchangeable cationic sites. Substantially cation exchange is preferred so that at least half of the cationic sites of the ion exchange zeolite contain a copper or silver cation. In one preferred embodiment, the majority of the cationic sites of the ion-exchanged zeolite contain silver cation. In an even more preferred embodiment, essentially all cationic sites of the ion-exchanged zeolite contain the silver cation.

Without being bound to any theory, it is believed that the preferential adsorption occurs by π-complexation.

The Cu-zeolites of the invention were prepared by ion exchanging with a solution of $CuCl_2$ or $Cu(NO_3)_2$, followed by reduction of $Cu^{+2}$ to $Cu^{+1}$.

In a preferred embodiment, the diene is selected from the group consisting of butadiene, hexadiene, octadiene and mixtures thereof. In an exemplary embodiment, the diene is 1,3-butadiene, and the mixture includes 1,3-butadiene and at least one other $C_4$ unsaturated compound. In a further exemplary embodiment, the mixture comprises at least one mono-olefin having as many carbon atoms as the diene, the diene is selected from the group consisting of butadiene, hexadiene, octadiene, and mixtures thereof; and the mono-olefin is selected from the group consisting of butene, hexene, octene, and mixtures thereof. In an exemplary example, the mono-olefin is butene and the diene is butadiene. The mono-olefin may be in a gaseous state and saturated with the diene.

The method may further comprise the step of changing at least one of the pressure and temperature to thereby release the diene-rich component from the adsorbent. In a preferred embodiment, the selected pressure of preferential adsorption is a first pressure, and the pressure of release is a second pressure less than the first pressure. In a more preferred embodiment, the first pressure is in a range of about 1 atmosphere to about 35 atmospheres, and the second pressure is in a range of about 0.01 atmosphere to about 5 atmospheres. Further, the selected temperature of preferential adsorption is a first temperature, and the temperature of release is a second temperature greater than the first temperature. In a preferred embodiment, the first temperature is in a range of about 0° C. to about 150° C., and the second temperature is in a range of about 70° C. to about 250° C.

This adsorbent also fortuitously and unexpectedly substantially maintains its adsorbent capacity and preference for the diene in the presence of the sulfur compound, for example, hydrogen sulfide.

In an alternate embodiment, a method is disclosed for separating a diene from a mixture including the diene and a sulfur compound. In an exemplary embodiment, the diene is selected from the group consisting of butadiene, hexadiene, octadiene, and mixtures thereof. The process comprises the step of contacting the mixture with an adsorbent which preferentially adsorbs the diene at a first temperature, thereby producing a non-adsorbed component and a diene-rich adsorbed component. The adsorbent comprises zeolite A having exchangeable cationic sites, a plurality of the zeolite A sites having an alkali metal cation or an alkaline earth metal cation present.

The method may further comprise the step of releasing the diene-rich adsorbed component from the adsorbent by elevating the temperature to a second temperature which ranges between about 70° C. and about 120° C.

In a preferred embodiment, a selected pressure of preferential adsorption is a first pressure, and a pressure of release is a second pressure less than the first pressure, wherein the first pressure is in a range of about 1 atmosphere to about 35 atmospheres, and the second pressure is in a range of about 0.01 atmosphere to about 5 atmospheres.

This adsorbent also fortuitously and unexpectedly substantially maintains its adsorbent capacity and preference for the diene in the presence of the sulfur compound.

As demonstrated below, the sulfur compound is generally hydrogen sulfide. The novel adsorbents were exposed to very severe amounts of hydrogen sulfide; for example the hydrogen sulfide was present in amounts up to about 66 mole %. In sharp contrast, a conventional cracked gas stream before any desulfurizing distillation steps contains hydrogen sulfide present in amounts of about 0.01 mole %. As such, the data presented hereinbelow indicate that the novel adsorbents of the present invention would be quite robust, i.e. very tolerant and/or resistant to $H_2S$ under normal operating conditions.

To further illustrate the present invention, the following examples are given. It is to be understood that these examples are provided for illustrative purposes and are not to be construed as limiting the scope of the present invention.

EXAMPLES

Effect of Sulfur Compounds on Olefin Selective Sorbents

Figure 2:
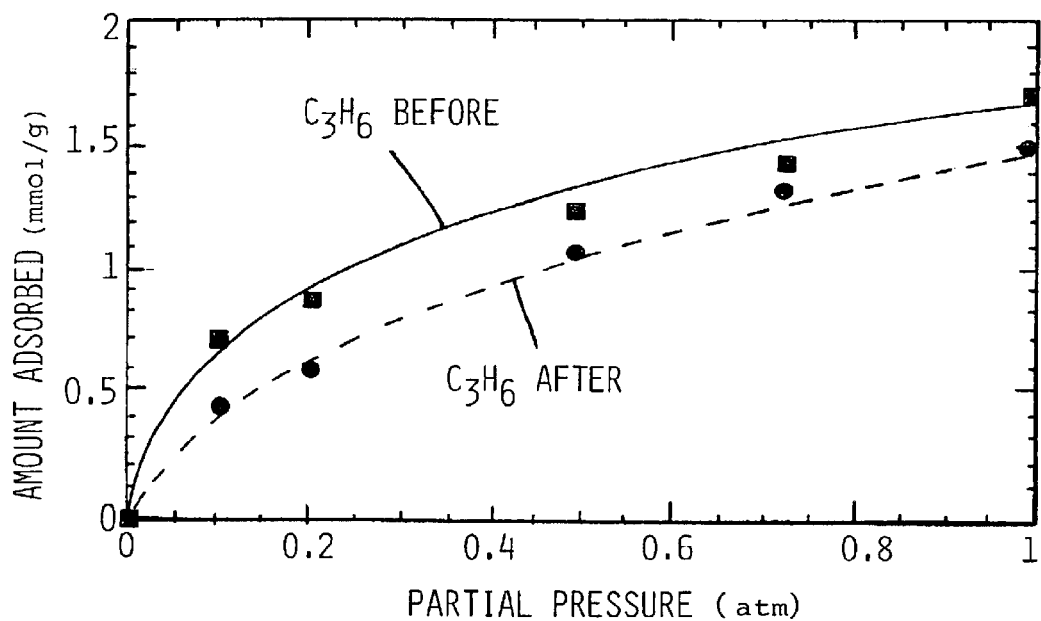
FIG. 2 is a graph showing $H_2S$ effect on olefin adsorption on $AgNO_3/SiO_2$.

In order to study the effect of sulfur compounds on the $AgNO_3/SiO_2$ sorbent, Hydrogen Sulfide ($H_2S$) was used as a model compound. Several isotherms of $H_2S$ were measured at 70° C. over $AgNO_3/SiO_2$ and $SiO_2$ sorbents and are shown in FIG. 1. $H_2S$ adsorption on $AgNO_3/SiO_2$ was mostly reversible with only about 0.04 mmol/g of $H_2S$ left on the surface. The effect of $H_2S$ on olefin adsorption on $AgNO_3/SiO_2$ can be observed in FIG. 2. After the sorbent was exposed to 1 atm of $H_2S$ at 70° C., $C_3H_6$ capacity at 1 atm and 70° C. was reduced from 1.6 to 1.5 mmol/g. This constituted a 6% reduction in $C_3H_6$ capacity. While it seems that the sorbent is affected negatively by the presence of $H_2S$, its effects were not as harmful as expected. Therefore, minimal or accidental exposure to sulfur compounds would not result in the total loss of the adsorption bed.

Silica gel is a very good sorbent for both olefins and paraffins, but it does not have selectivity (about 1.1) for one as opposed to the other. In the presence of $H_2S$, it can be seen that the inventive sorbent(s) have about the same selectivity as they had before exposure to $H_2S$. One can conclude from this that the hydrocarbons are fortuitously adsorbing even on sulfur covered surfaces.

In the following cycling studies many ethylene and propylene adsorption cycles were run on $AgNO_3/SiO_2$. There was virtually no capacity loss below 50° C. $AgNO_3/SiO_2$ has been demonstrated to be very stable, and this is a highly favorable aspect of the adsorbent.

Cycling Studies

Figure 3:
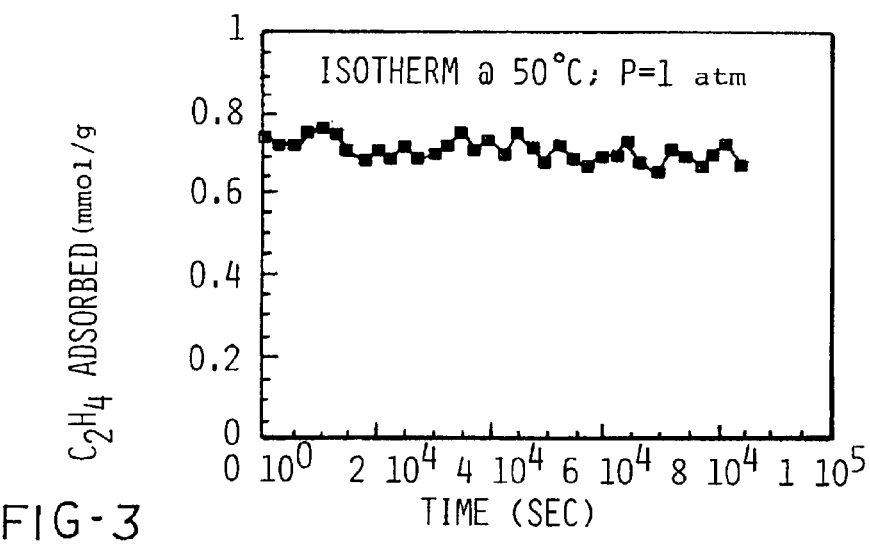
FIG. 3 is a graph showing $C_2H_4$ cyclic adsorption on $AgNO_3/SiO_2$ at 50° C.
Figure 4:
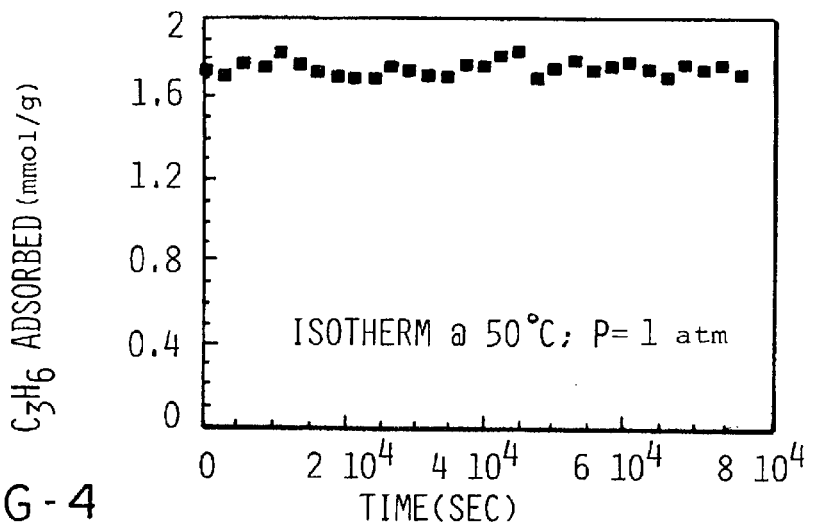
FIG. 4 is a graph showing $C_3H_6$ cyclic adsorption on $AgNO_3/SiO_2$ at 50° C.

These are simply many adsorption experiments repeated continuously using the same adsorbent. The data correspond to 80 cycles of 20 minutes each. A straight, horizontal line on the plot means that the equilibrium loading is the same for every cycle. This suggests that the $Ag^+$ remains fully active on the adsorbent throughout the service life. The 50° C. graphs (FIGS. 3 and 4) for $C_2H_4$ and $C_3H_6$ are not exactly horizontal, although they do show a consistent loading range throughout many cycles.

Figure 5:
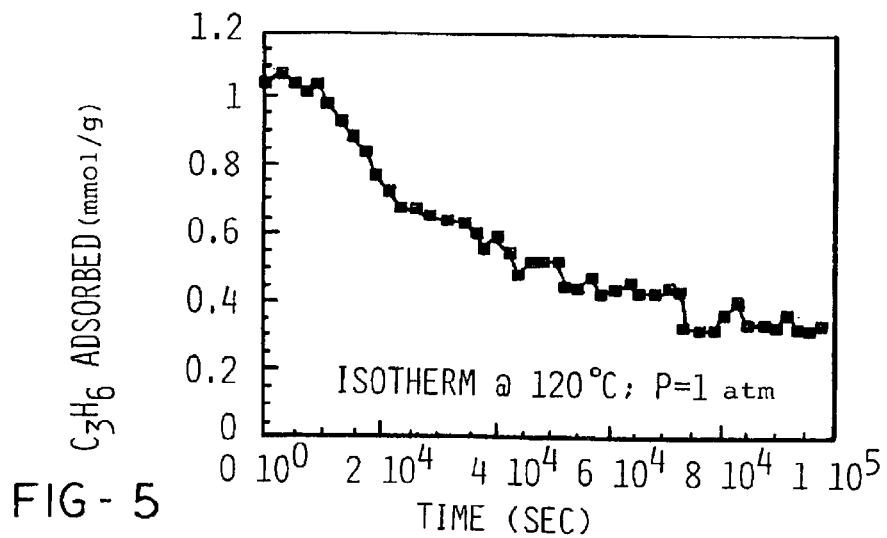
FIG. 5 is a graph showing $C_3H_6$ cyclic adsorption on $AgNO_3/SiO_2$ at 120° C.

The 120° C. data (FIG. 5) for $C_3H_6$ however, shows that loading begins to decrease sharply initially, and then to a new plateau. The loss of capacity likely suggests that some of the $Ag^+$ sites are somehow losing activity. High temperatures usually accelerate the rate of degradation for all adsorbents in general.

Figure 6:
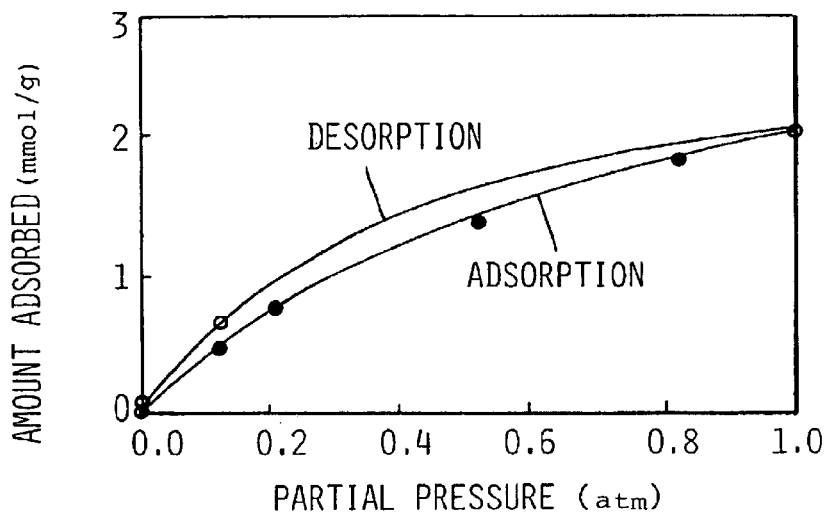
FIG. 6 is a graph showing $H_2S$ adsorption and desorption on $SiO_2$ at 298K.
Figure 7:
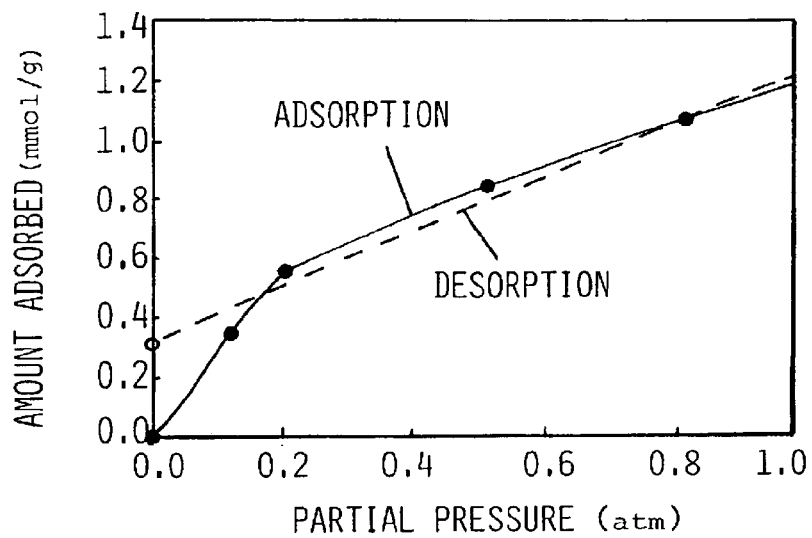
FIG. 7 is a graph showing $H_2S$ adsorption and desorption on $AgNO_3/SiO_2$ at 298K.
Figure 8:
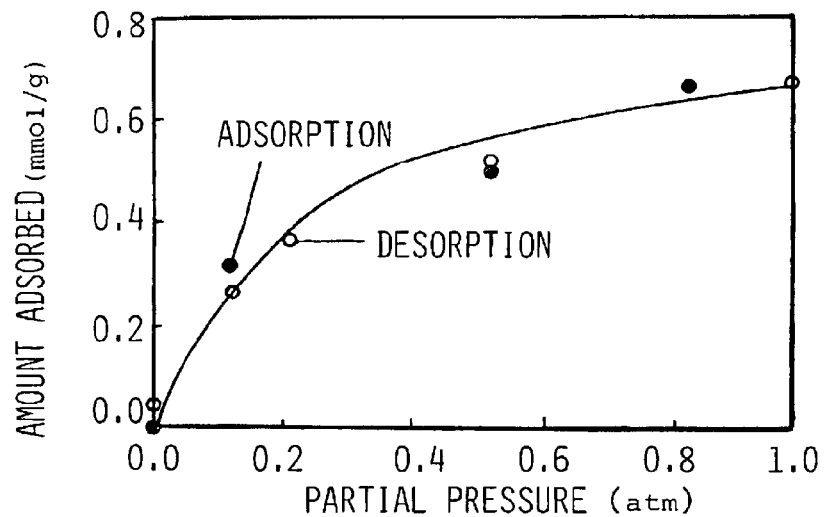
FIG. 8 is a graph showing $H_2S$ adsorption and desorption on $AgNO_3/SiO_2$ at 343K.
Figure 9:
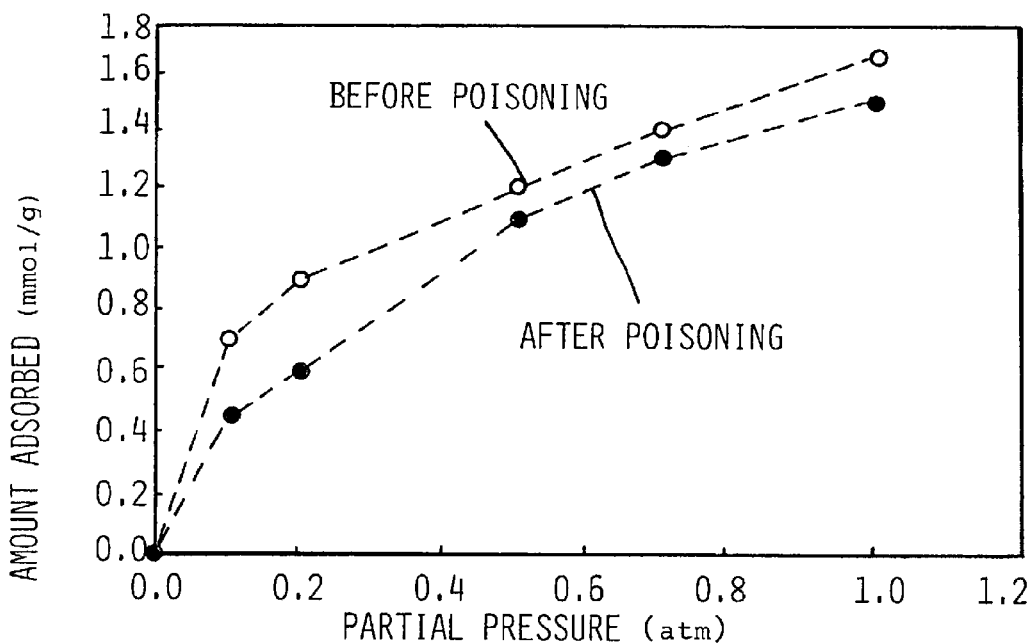
FIG. 9 is a graph showing the effect of $H_2S$ poisoning on $AgNO_3/SiO_2$ capacity for $C_3H_6$ at 343K.
Figure 11:
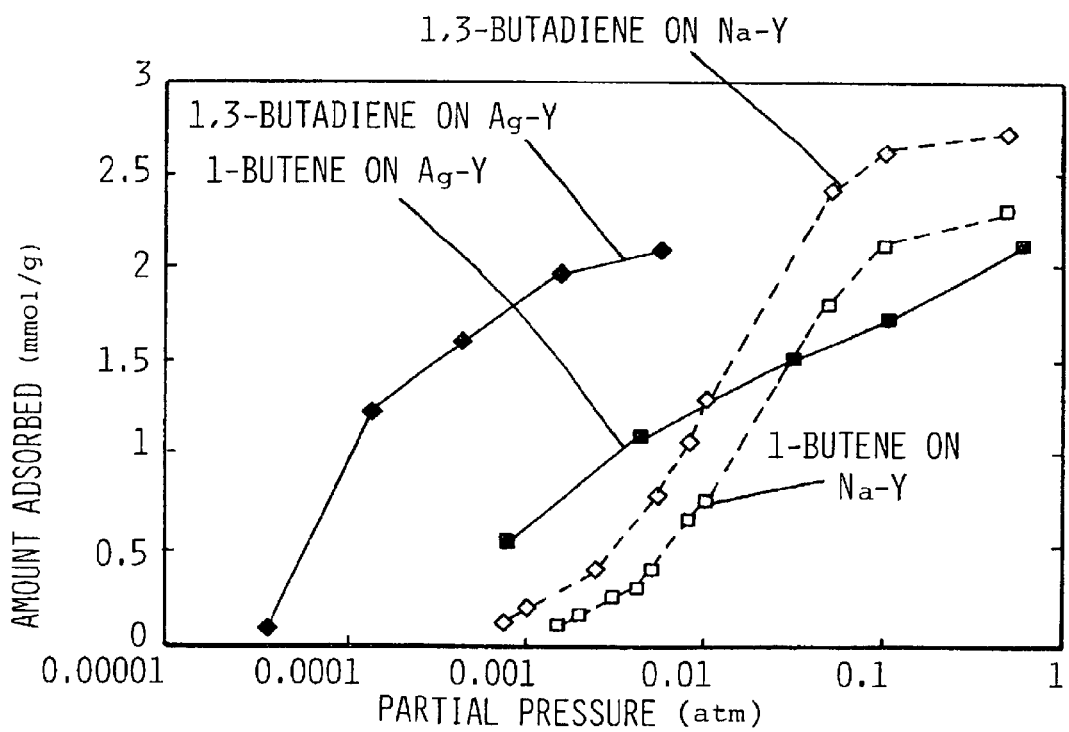
FIG. 11 is a graph showing Ag—Y after $H_2S$ exposure vs. Na—Y before $H_2S$ exposure.
Figure 10B:
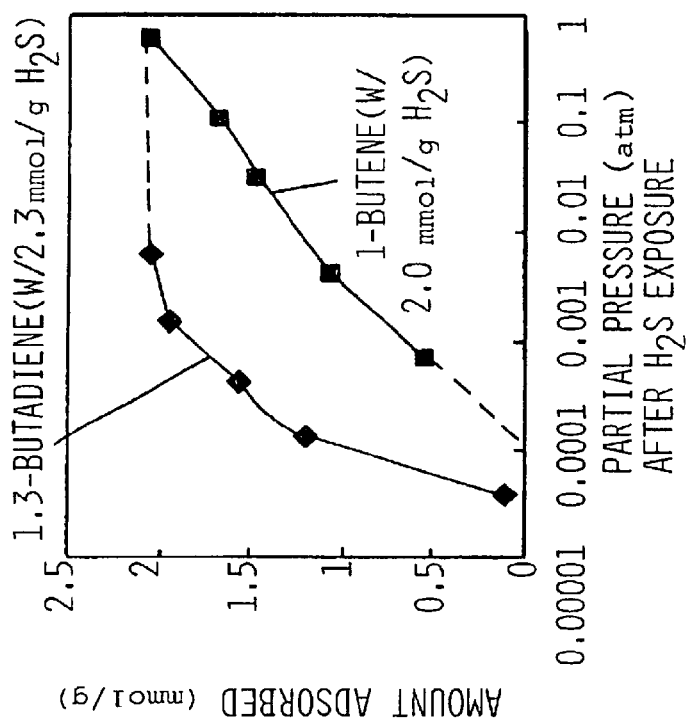
FIGS. 10a and 10b are graphs showing isotherms of 1,3-butadiene and 1-butene at 120° C. before and after $H_2S$ exposure.
Figure 10A:
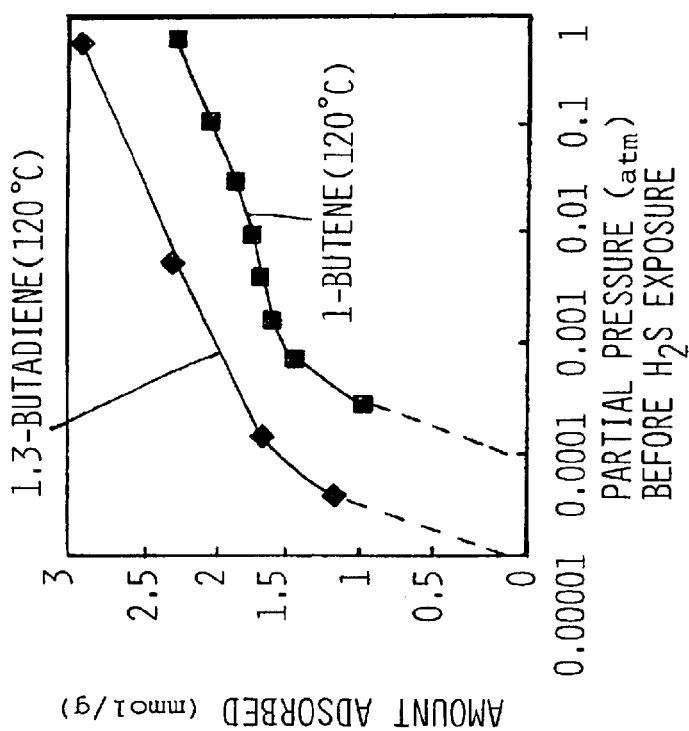
Figure 13:
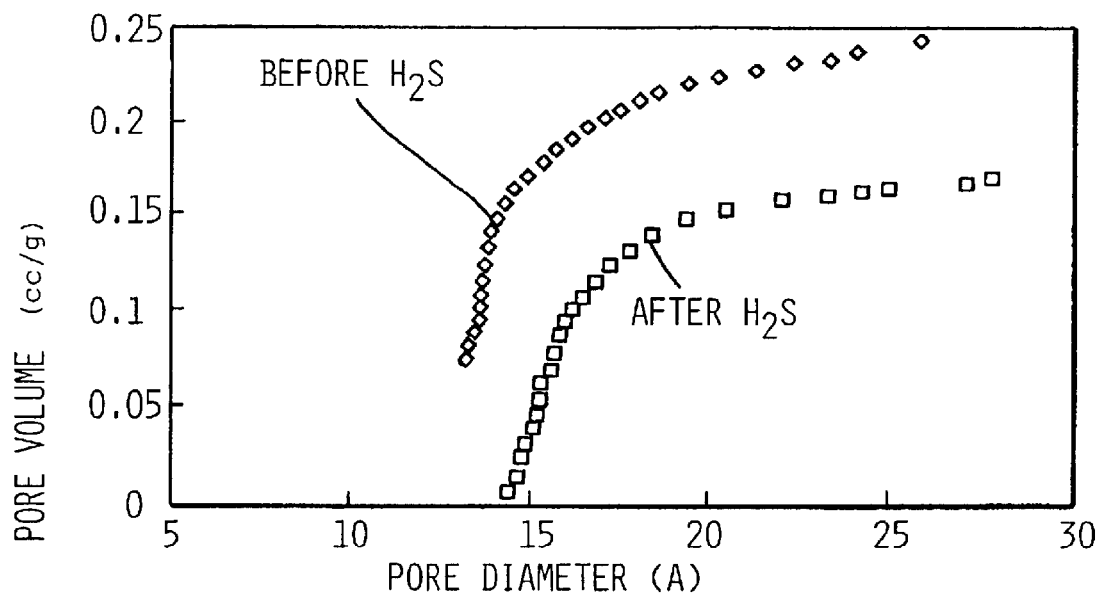
FIG. 13 is a graph showing cumulative pore volume of Ag—Y before and after $H_2S$ exposure.
Figure 14A:
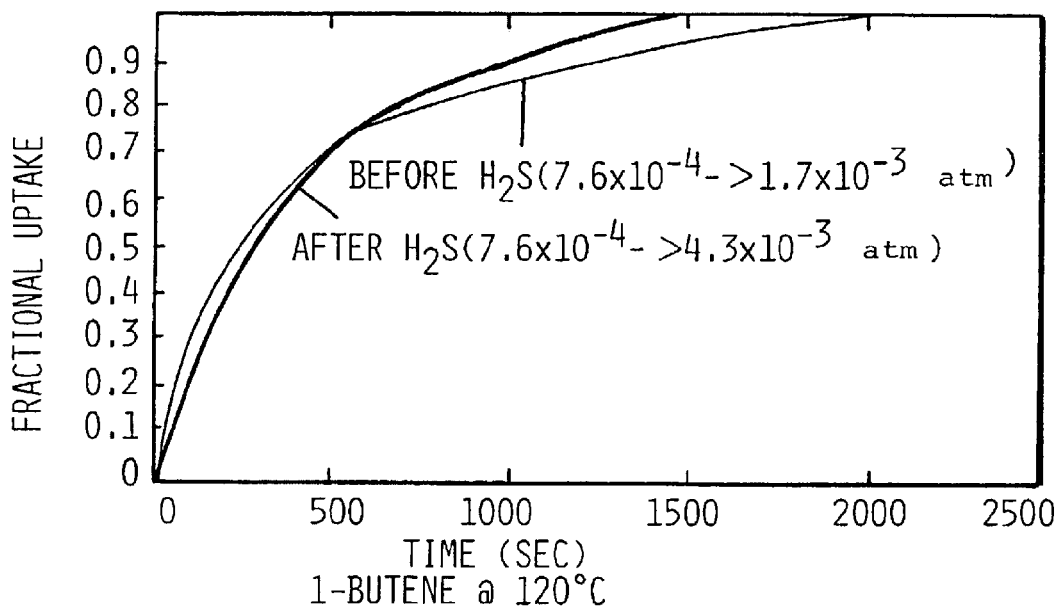
FIGS. 14a and 14b are fractional uptake curves of 1-butene and 1,3-butadiene before and after $H_2S$ exposure.
Figures 14B, 14C:
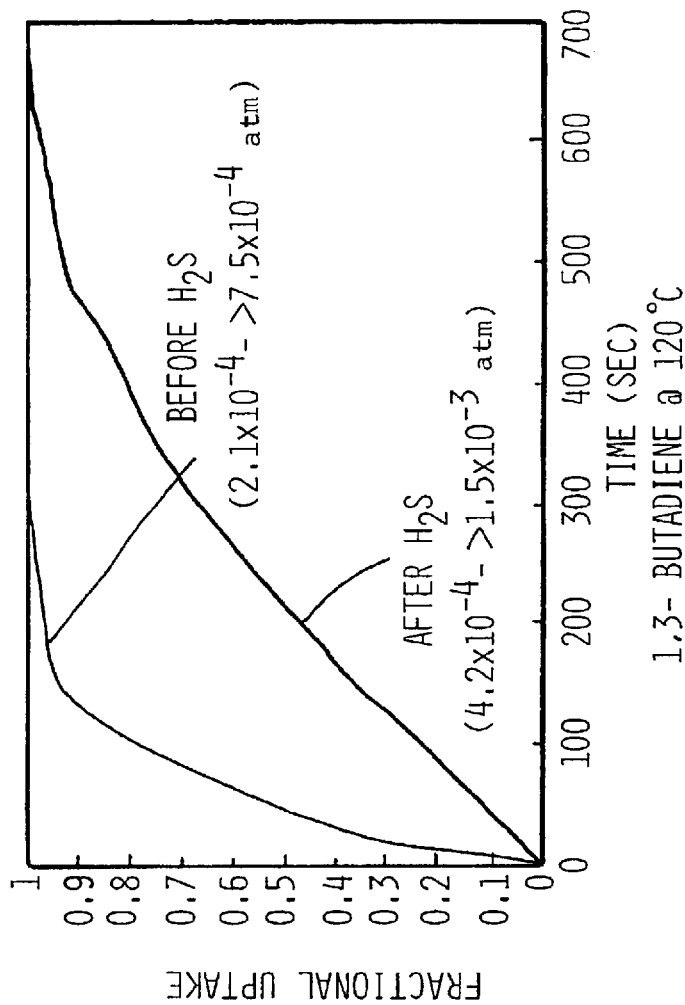
FIG. 14c is a table showing diffusion time constants (1/s) for 1,3-butadiene and 1-butene before and after $H_2S$ exposure.

$H_2S$ Adsorption/Desorption on $AgNO_3/SiO_2$ $C_3H_6$ has been shown to be readsorbed at 70° C. onto a $AgNO_3/SiO_2$ adsorbent that was previously exposed to 1 atm of $H_2S$. As shown in the earlier graphs, it appears that a substantial portion of the $H_2S$ desorbs upon lowering the pressure. See FIGS. 6–8. The "poisoned" adsorbent thus refers to adsorbent containing residual $H_2S$ that is adsorbed irreversibly. From the $C_3H_6$ data (FIG. 9), we see that the capacity has diminished only slightly.

Figure 15:
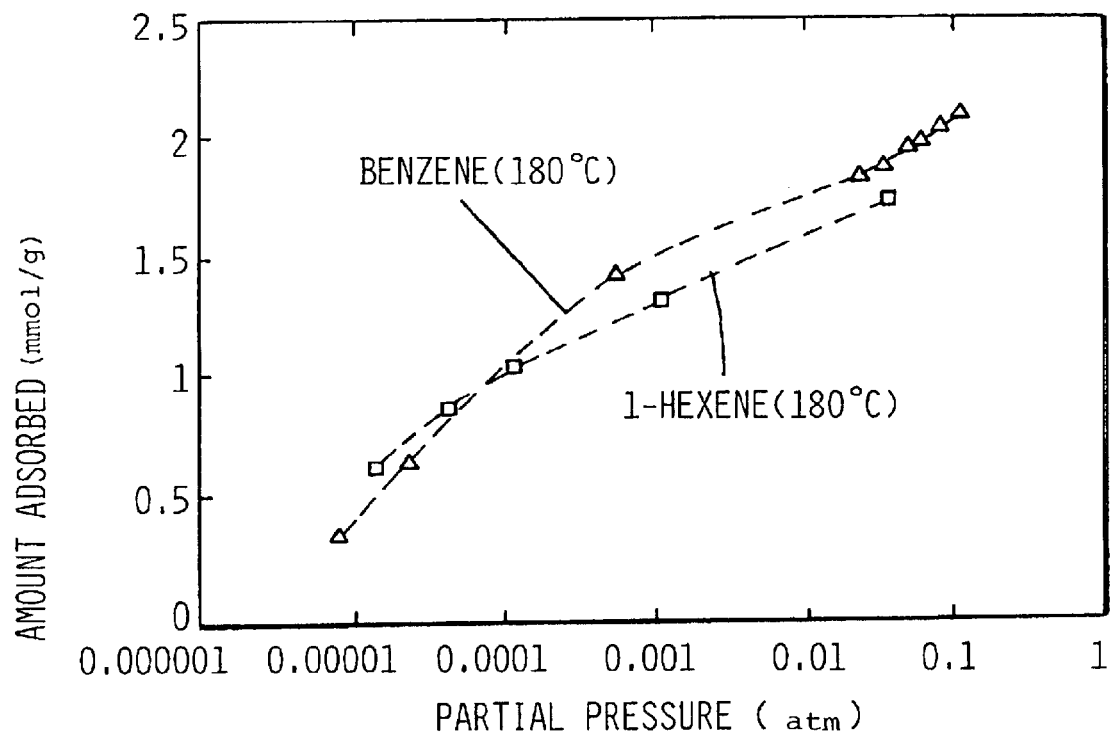
FIG. 15 is a graph showing an isotherm of benzene and 1-hexene on Ag—Y.

Sorbent for Purification of 1-Hexene by Removal of Benzene See FIG. 15

Effects of $H_2S$ on Ag—Y Zeolite for 1,3-Butadiene/1-Butene Adsorption

Some $H_2S$ is adsorbed on Ag—Y irreversibly. However, purification capability of Ag—Y was maintained by shifting the adsorption of both adsorbates to higher pressure. See FIGS. 10–14.

Purification of butene by removal of trace amounts of butadiene was successfully achieved at Chevron by using Ag ion-exchanged zeolite (Ag—Y). In an actual purification process, certain amounts of $H_2S$ and $H_2$ may be present in the process stream. In this report, the effect of $H_2S$ exposure on butadiene/butene adsorption will be examined.

Experimental

Ag—Y(Si/Al=2.43) was prepared by the ion exchange of Na—Y (Si/Al=2.43, Strem Chemical) in excess amounts of Ag cations. First the gas phase adsorption isotherms of $H_2S$ were measured at 25–180° C. using a gravimetric method (SHIMADZU TGA-50) in order to understand the reversibility of $H_2S$ adsorption on Ag—Y. Then, isotherms of 1,3-butadiene and 1-butene on Ag—Y were examined before and after $H_2S$ exposure. The sorbent was subjected to $H_2S$ exposure at 0.66 atm for 10 minutes at either room temperature or 120° C., which is extremely severe compared to the actual level of $H_2S$ present in the process stream, so that the effect on the sorbent after long time usage can be understood.

Results and Discussion

Figure 16:
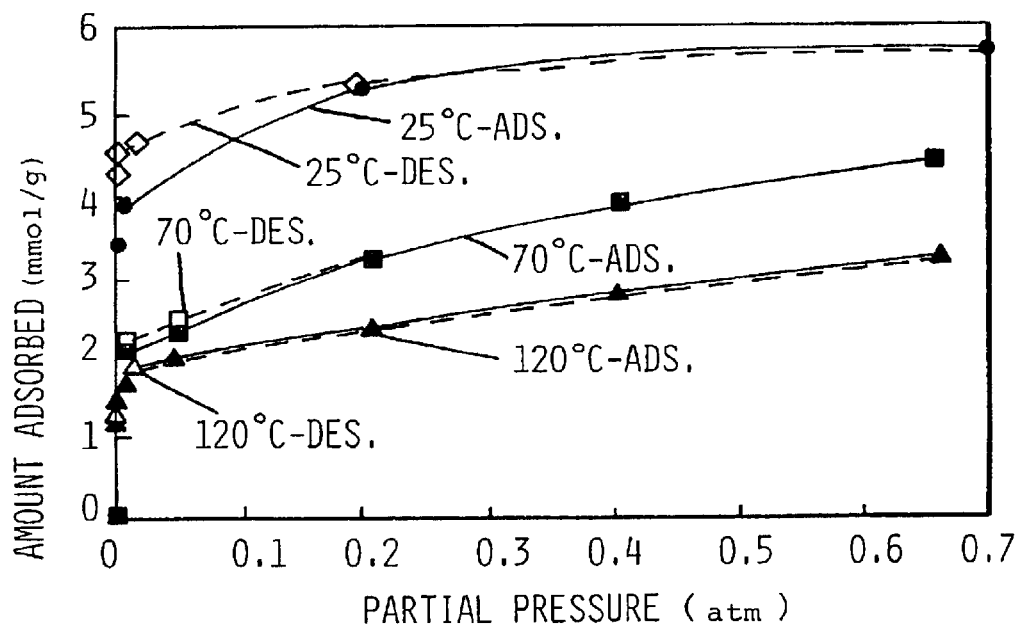
FIG. 16 is a graph showing $H_2S$ isotherms on Ag—Y.

Adsorption and desorption isotherms of $H_2S$ on Ag—Y at 25° C., 70° C. and 120° C. are shown in FIG. 16. It was found that $H_2S$ was irreversibly adsorbed on Ag—Y at lower pressure ranges less than 0.2 atm. Also, a fairly large amount of $H_2S$ was adsorbed on Ag—Y even at a low pressure of $7 \times 10^{-4}$ atm. At 180° C. (not shown here), the weight of Ag—Y in the TGA-50 increased continuously in the presence of $H_2S$. These results indicate a reaction between Ag—Y and $H_2S$ occurred at 180° C. and even at lower temperatures such as 25–120° C. One possible reaction is the formation of $Ag_2S$. Actually, the color of Ag—Y changed from white to dark brown, which is the color of $Ag_2S$. Analytical investigation such as XPS (X-ray Photoelectron Spectroscopy) would be helpful to understand the reaction products.

Figure 17:
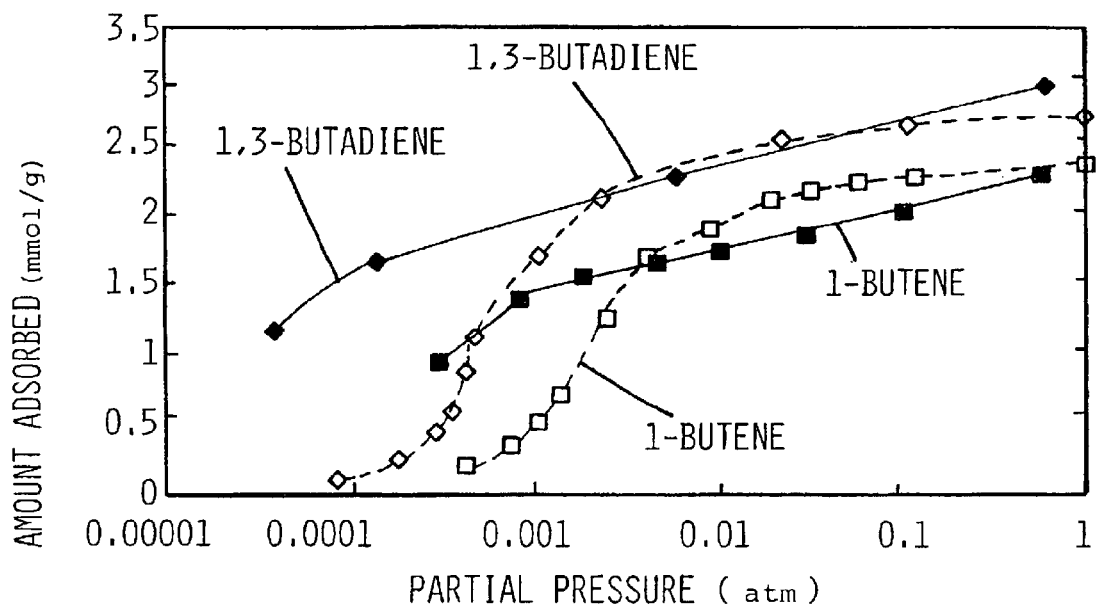
FIG. 17 is a graph showing isotherms of $C_4H_6$ and $C_4H_8$ on Ag—Y at 120° C.

Adsorption isotherms of 1,3-butadiene and 1-butene are plotted in FIG. 17, compared with isotherms of the adsorbates for the novel adsorbents having not been exposed to $H_2S$ (labelled "Joel et al."). Isotherms of both adsorbates in the present invention have a lower threshold pressure than those labelled "Joel et al." The threshold pressure is the value where the steep rise in the isotherm occurs. At present, the reason for this difference is not clear except the sample preparation conditions were slightly different. However, based on the results in FIG. 17, the sorbent in this work is also useful for purification of butene by removal of butadiene and was used for further studies on the $H_2S$ effect.

Figure 18:
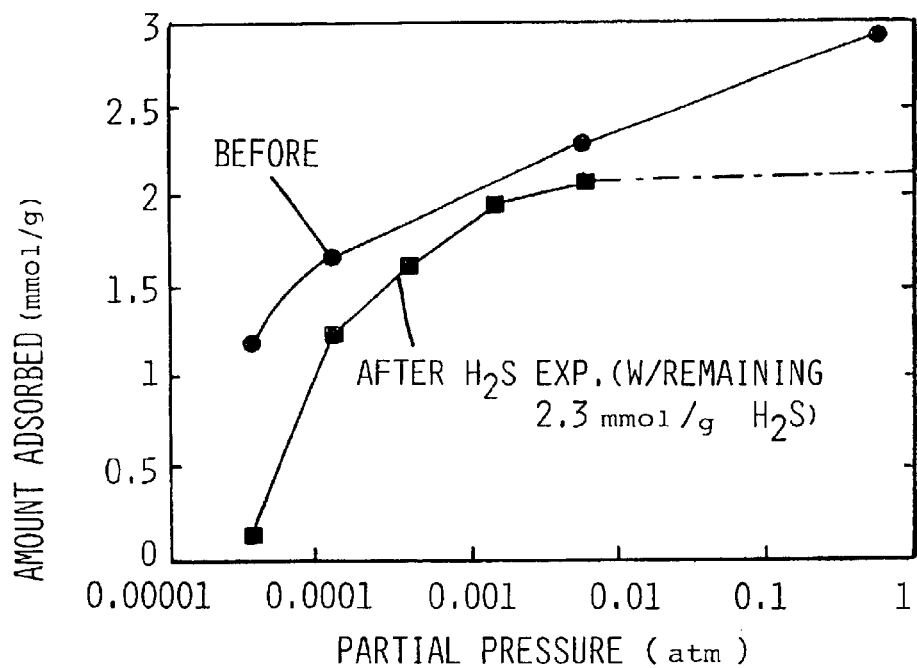
FIG. 18 is a graph showing isotherms of 1,3-butadiene before and after $H_2S$ exposure at 120° C.
Figure 19:
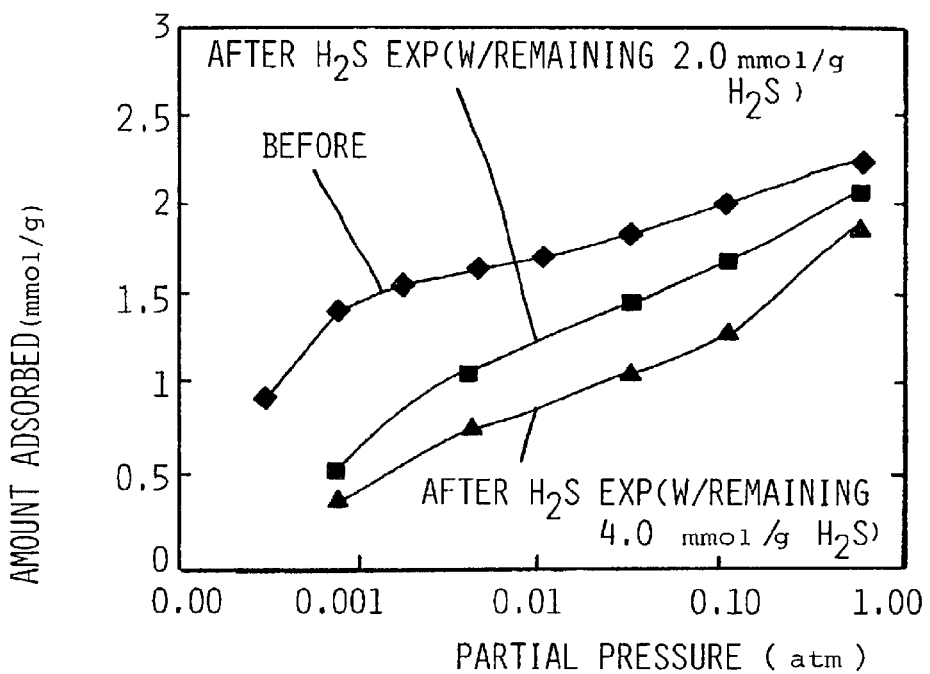
FIG. 19 is a graph showing isotherms of 1-butene before and after $H_2S$ exposure at 120° C.
Figure 20:
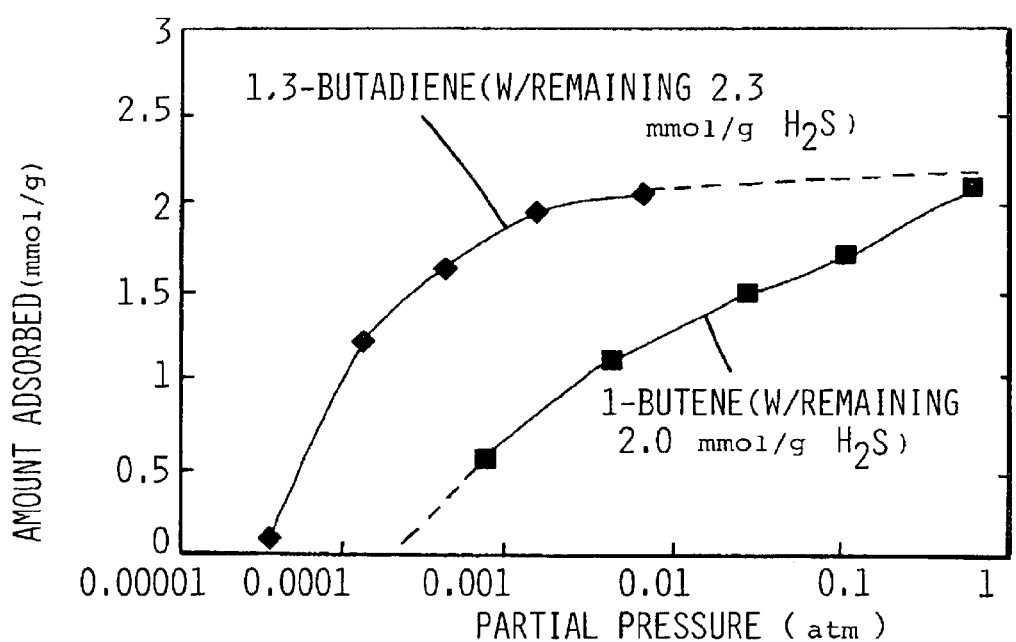
FIG. 20 is a graph showing isotherms of 1-butene and 1,3-butadiene after $H_2S$ exposure.

The effect of $H_2S$ on adsorption isotherms of butadiene and butene are examined in FIGS. 18 and 19, respectively. Irreversible $H_2S$ adsorption amounts after $H_2S$ exposure are indicated in the figures. In both cases, adsorption amounts at the same partial pressure were decreased. And the partial pressures of adsorbates for the same adsorption amounts were shifted to higher pressures by $H_2S$ exposure. However, it was clearly demonstrated that Ag—Y sorbent maintained its purification capability even after this severe $H_2S$ exposure test as shown in FIG. 20, which compares isotherms of Ag—Y containing 2.0–2.3 mmol/g of irreversibly adsorbed $H_2S$.

Although some $H_2S$ appeared to be irreversibly adsorbed on Ag—Y, purification capability of Ag—Y was maintained by shifting the adsorption of both adsorbates to higher pressures.

In conclusion, as stated above, $H_2S$ is always present to some extent in cracked gas streams. It is typically removed with conventional technology prior to the olefin-paraffin separation step. In the case of $Ag^+$-based systems (eg. the classical, aqueous $AgNO_3$ adsorption systems), the presence of $H_2S$ leads to loss of silver ions through the formation of silver sulfide, $Ag_2S$. This reaction between $H_2S$ and $Ag^+$ ions in water is known to occur very readily. The $Ag_2S$ formed is a finely-divided precipitate that is highly insoluble in water. The room temperature solubility of $AgNO_3$ in water is 216 g/L, while that of $Ag_2S$ is $1.4 \times 10^{-4}$ g/L. Therefore, for solid adsorbents containing monodispersed or ion-exchanged $Ag^+$, one would expect a similar sulfide-forming reaction to occur with $H_2S$. That is, some or all of the $Ag^+$ will likely "come off" of the adsorbent as $Ag_2S$ particles. The effectiveness of the adsorbent for olefins should therefore be greatly reduced.

The present inventive findings are unexpected and remarkable in this regard. From the collected data, there is evidence that some $H_2S$ adsorbs irreversibly onto AgY and $AgNO_3/SiO_2$. However, it appears that the adsorbents still have sufficient capacity and selectivity for olefins over paraffins. Without being bound to any theory, it is believed that the reason for this may be that the silver in the "poisoned" $Ag_2S$ sites are sufficiently "ionic" so that they are in the $^+1$ state, and thus able to pi-complex with olefins.

While preferred embodiments of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. A method of separating gaseous alkene selected from the group consisting of ethylene, propylene and mixtures thereof, from a gaseous mixture including the alkene and a sulfur, the hydrogen sulfide present in amounts normally present in conventional cracked gas streams, the method comprising the steps of:

contacting the gaseous mixture with an adsorbent which preferentially adsorbs the alkene, at a selected temperature and pressure, thereby producing a non-adsorbed component and an alkene-rich adsorbed component; the adsorbent comprising a carrier having a surface area, the carrier having a monolayer of a silver compound dispersed on substantially the entire surface area, the silver compound releasably retaining the alkene; and the carrier comprising a plurality of pores having a pore size greater than the effective molecular diameter of the alkene; and changing at least one of the pressure and temperature to thereby release the alkene-rich component from the adsorbent;

wherein the adsorbent substantially maintains its adsorbent capacity and preference for the alkene in the presence of the hydrogen sulfide.

2. The method as defined in claim 1 wherein the silver compound comprising silver nitrate ($AgNO_3$), and the carrier is silica ($SiO_2$).

3. The method as defined in claim 1 wherein the silver compound comprising a silver salt, and wherein the salt is selected from the group consisting of acetate, benzoate, bromate, chlorate, perchlorate, chlorite, citrate, fluoride, nitrate, nitrite, sulfate, and mixtures thereof.

4. The method as defined in claim 1 wherein the carrier has a BET surface area greater than about 50 square meters per gram and up to about 2,000 square meters per gram, and comprises a plurality of pores having a pore size greater than about 3 angstroms and up to about 10 microns.

5. The method as defined in claim 1 wherein the carrier is a high surface area support selected from the group consisting of refractory inorganic oxide, molecular sieve, activated carbon, and mixtures thereof.

6. The method as defined in claim 5 wherein the refractory inorganic oxide is selected from the group consisting of pillared clay, alumina and silica.

7. The method as defined in claim 1 wherein the silver compound comprising a silver (I) halide, and the carrier is silica.

8. The method as defined in claim 1 wherein the selected pressure of preferential adsorption is a first pressure, and the pressure of release is a second pressure less than the first pressure, and wherein the first pressure is in a range of about 1 atmosphere to about 35 atmospheres, and further wherein the second pressure is in a range of about 0.01 atm to about 5 atm.

9. The method as defined in claim 1 wherein the selected temperature of preferential adsorption is a first temperature, and the temperature of release is a second temperature greater than the first temperature, and wherein the first temperature is in a range of about O° C. to about 50° C., and further wherein the second temperature is in a range of about 70° C. to about 200° C.

10. The method as defined in claim 1 wherein the retaining of the alkene is accomplished by formation of π-complexation bonds between the silver compound and the alkene.

11. A method for separating a diene from a mixture including the diene and hydrogen sulfide, the hydrogen sulfide present in amounts normally present in conventional cracked gas streams, the method comprising the step of:
contacting the mixture with an adsorbent which preferentially adsorbs the diene, at a selected temperature and pressure, thereby producing a non-adsorbed component and a diene-rich adsorbed component, wherein the adsorbent comprises an ion-exchanged zeolite selected from the group consisting of zeolite X, zeolite Y, zeolite LSX, and mixtures thereof, the zeolite having exchangeable cationic sites, and a majority of the sites having silver cation or copper cation present, and wherein the preferential adsorption occurs by π-complexation, and further wherein the adsorbent substantially maintains its adsorbent capacity and preference for the diene in the presence of the hydrogen sulfide.

12. The method as defined in claim 11 wherein the diene is selected from the group consisting of butadiene, hexadiene, octadiene and mixtures, thereof, and wherein the method further comprises the step of changing at least one of the pressure and temperature to thereby release the diene rich component from the adsorbent.

13. The method as defined in claim 11 wherein the diene is 1,3-butadiene, and wherein the mixture includes 1,3-butadiene and at least one other $C_4$ unsaturated compound.

14. The method as defined in claim 11 wherein the majority of the cationic sites of the ion-exchanged zeolite contain the silver cation.

15. The method as defined in claim 11 wherein the majority of the cationic sites of the ion-exchanged zeolite contain the copper cation.

16. The method as defined in claim 11 wherein the mixture comprises at least one mono-olefin having as many carbon atoms as the diene, wherein the diene is selected from the group consisting of butadiene, hexadien, octadiene, and mixtures thereof; and wherein the mono-olefin is selected from the group consisting of butene, hexene, octene, and mixtures thereof.

17. The method as defined in claim 16 wherein the mono-olefin is butene and the diene is butadiene.

18. The method as defined in claim 16 wherein the mixture comprises the mono-olefin in a gaseous state and saturated with the diene.

19. The method as defined in claim 11 wherein essentially all cationic sites of the ion-exchanged zeolite contain the silver cation.

20. The method as defined in claim 12 wherein the selected pressure of preferential adsorption is a first pressure, and the pressure of release is a second pressure less than the first pressure, wherein the first pressure is in a range of about 1 atmosphere to about 35 atmosphere, and wherein the second pressure is in a range of about 0.01 atmosphere to about 5 atmospheres.

21. The method as defined in claim 12 wherein the selected temperature of preferential adsorption is a first temperature, and the temperature of release is a second temperature greater than the first temperature, wherein the first temperature is in a range of about O° C. to about 150° C., and wherein the second temperature is in a range of about 70° C. to about 250° C.

22. A method of separating gaseous alkene selected from the group consisting of ethylene, propylene and mixtures thereof, from a gaseous mixture including the alkene and a sulfur compound, the method comprising the steps of:
contacting the gaseous mixture with an adsorbent which preferentially adsorbs the alkene, at a selected temperature and pressure, thereby producing a non-adsorbed component and an alkene-rich adsorbed component; the adsorbent comprising a carrier having a surface area, the carrier having a monolayer of a silver compound dispersed on substantially the entire surface area, the silver compound releasably retaining the alkene; and the carrier comprising a plurality of pores having a pore size greater than the effective molecular diameter of the alkene; and
changing at least one of the pressure and temperature to thereby release the alkene-rich component from the adsorbent;
wherein the adsorbent substantially maintains its adsorbent capacity and preference for the alkene in the presence of the sulfur compound, wherein the sulfur compound is hydrogen sulfide, and wherein the hydrogen sulfide is present in amounts up to about 66 mole %.

23. The method as defined in claim 11 wherein the hydrogen sulfide is present in amounts up to about 66 mole %.

24. A method for separating a diene from a mixture including the diene and hydrogen sulfide, the hydrogen sulfide present in amounts normally present in conventional cracked gas streams, the method comprising the step of:
contacting the mixture with an adsorbent which preferentially adsorbs the diene, at a selected temperature and pressure, thereby producing a non-adsorbed component and a diene-rich adsorbed component, wherein the adsorbent comprises an ion-exchanged zeolite selected from the group consisting of zeolite X, zeolite Y, zeolite LSX, and mixtures thereof, the zeolite having exchangeable cationic sites, and at least some of the sites having silver cation or copper cation present, and wherein the preferential adsorption occurs by π-complexation, and further wherein the adsorbent substantially maintains its adsorbent capacity and preference for the diene in the presence of the hydrogen sulfide.

25. The method as defined in claim 24 wherein the diene is selected from the group consisting of butadiene, hexadiene, octadiene and mixtures thereof, and wherein the method further comprises the step of changing at least one of the pressure and temperature to thereby release the diene-rich component from the adsorbent.

26. The method as defined in claim 24 wherein the diene is 1,3-butadiene, and wherein the mixture includes 1,3-butadiene and at least one other $C_4$ unsaturated compound.

27. The method as defined in claim 24 wherein a majority of the cationic sites of the ion-changed zeolite contain the silver cation.

28. The method as defined in claim 24 wherein a majority of the cationic sites of the ion-exchanged zeolite contain the copper cation.

29. The method as defined in claim 24 wherein the mixture comprises at least one mono-olefin having as many carbon atoms as the diene, wherein the diene is selected from the group consisting of butadiene, hexadiene, octadiene, and mixtures thereof; and wherein the mono-olefin is selected from the group consisting of butene, hexene, octene, and mixtures thereof.

30. The method as defined in claim 29 wherein the mono-olefin is butene and the diene is butadiene.

31. The method as defined in claim 29 wherein the mixture comprises the mono-olefin in a gaseous state and saturated with the diene.

32. The method as defined in claim 24 wherein essentially all cationic sites of the ion-exchanged zeolite contain the silver cation.

33. The method as defined in claim 25 wherein the selected pressure of preferential adsorption is a first pressure, and the pressure of release is a second pressure less than the first pressure, wherein the first pressure is in a range of about 1 atmosphere to about 35 atmospheres, and wherein the second pressure is in a range of about 0.01 atmosphere to about 5 atmospheres.

34. The method as defined in claim 25 wherein the selected temperature of preferential adsorption is a first temperature, and the temperature of release is a second temperature greater than the first temperature, wherein the first temperature is in a range of about 0° C. to about 150° C., and wherein the second temperature is in a range of about 70° C. to about 250° C.

35. The method as defined in claim 24 wherein the at least some of the sites have silver cation present.

36. The method as defined in claim 24 wherein the at least some of the sites have copper cation present.

37. The method as defined in claim 24 wherein essentially all cationic sites of the ion-exchanged zeolite contain the copper cation.

38. A method for separating a diene from a mixture including the diene and hydrogen sulfide, the hydrogen sulfide present in amounts normally present in conventional cracked gas streams, wherein the diene is selected from the group consisting of butadiene, hexadiene, octadiene and mixtures thereof, wherein the mixture comprises at least one mono-olefin having as many carbon atoms as the diene, and wherein the mono-olefin is selected from the group consisting of butene, hexane, octene, and mixtures thereof, the method comprising the steps of:

contacting the mixture with an adsorbent which preferentially adsorbs the diene, at a selected temperature and pressure, thereby producing a non-adsorbed component and a diene-rich adsorbed component, wherein the adsorbent comprises an ion-exchanged zeolite selected from the group consisting of zeolite X, zeolite Y, zeolite LSX, and mixtures thereof, the zeolite having exchangeable cationic sites, and at least some of the sites having silver cation or copper cation present, and wherein the preferential adsorption occurs by π-complexation, and further wherein the adsorbent substantially maintains its absorbent capacity and preference for the diene in the presence of the hydrogen sulfide;

changing at least one of the pressure and temperature to thereby release the diene-rich component from the adsorbent, wherein the selected pressure of preferential adsorption is a first pressure, and the pressure of release is a second pressure less than the first pressure, wherein the first pressure is in a range of about 1 atmosphere to about 35 atmospheres, and wherein the second pressure is in a range of about 0.01 atmosphere to about 5 atmospheres;

and wherein the selected temperature of preferential adsorption is a first temperature, and the temperature of release is a second temperature greater than the first temperature, wherein the first temperature is in a range of about 0° C. to about 150° C., and wherein the second temperature is in a range of about 70° C. to about 250° C.

39. The method as defined in claim 38 wherein the mono-olefin is butene and the diene is butadiene.

40. The method as defined in claim 38 wherein the mixture comprises the mono-olefin in a gaseous state and saturated with the diene.

41. The method as defined in claim 38 wherein a majority of the sites have silver cation present.

42. The method as defined in claim 38 wherein a majority of the sites have copper cation present.

43. The method as defined in claim 38 wherein essentially all cationic sites of the ion-exchanged zeolite contain the copper cation.

44. The method as defined in claim 38 wherein essentially all cationic sites of the ion-exchanged zeolite contain the silver cation.

45. The method as defined in claim 1 wherein the gaseous mixture is contained in a conventional cracked gas stream before any desulfurizing distillation steps.

46. The method as defined in claim 11 wherein the gaseous mixture is contained in a conventional cracked gas stream before any desulfurizing distillation steps.

47. The method as defined in claim 24 wherein the gaseous mixture is contained in a conventional cracked gas stream before any desulfurizing distillation steps.

48. The method as defined in claim 38 wherein the gaseous mixture is contained in a conventional cracked gas stream before any desulfurizing distillation steps.

* * * * *